(12) United States Patent
Fenton

(10) Patent No.: US 8,857,432 B2
(45) Date of Patent: Oct. 14, 2014

(54) VENTILATING ELEMENT, SYSTEM, AND METHODS

(75) Inventor: Paul Fenton, Agnac (FR)

(73) Assignee: Gradian Health Systems LLC, New York, NY (US)

( * ) Notice: Subject to any disclaimer, the term of this patent is extended or adjusted under 35 U.S.C. 154(b) by 369 days.

(21) Appl. No.: 12/953,655

(22) Filed: Nov. 24, 2010

(65) Prior Publication Data
US 2011/0203589 A1   Aug. 25, 2011

Related U.S. Application Data

(60) Provisional application No. 61/307,066, filed on Feb. 23, 2010.

(51) Int. Cl.
*A61M 16/00* (2006.01)
*A61M 16/01* (2006.01)

(52) U.S. Cl.
CPC ....... *A61M 16/0075* (2013.01); *A61M 16/0084* (2014.02); *A61M 16/01* (2013.01); *A61M 16/0072* (2013.01)
USPC ............. 128/205.14; 128/205.13; 128/205.17

(58) Field of Classification Search
USPC .......................... 128/204.18, 203.28, 204.28, 128/205.12–205.17; 604/95.03, 216
See application file for complete search history.

(56) References Cited

U.S. PATENT DOCUMENTS

| | | | |
|---|---|---|---|
| 2,399,643 A * | 5/1946 | Kreiselman | 128/205.13 |
| 2,428,451 A * | 10/1947 | Emerson | 128/205.13 |
| 2,737,177 A * | 3/1956 | Anklin | 128/205.13 |
| 2,766,753 A | 10/1956 | Koch et al. | |
| 4,297,999 A | 11/1981 | Kitrell | |
| 4,498,472 A * | 2/1985 | Tanaka | 128/205.17 |
| 4,821,713 A * | 4/1989 | Bauman | 128/205.13 |
| 4,870,962 A | 10/1989 | Sitnik | |
| 4,898,167 A | 2/1990 | Pierce et al. | |
| 4,934,360 A | 6/1990 | Heilbron et al. | |
| 5,006,376 A * | 4/1991 | Arima et al. | 277/636 |
| 5,052,384 A | 10/1991 | Kaneko | |
| 5,109,833 A | 5/1992 | Frimberger | |
| 5,285,775 A | 2/1994 | Mayer | |

(Continued)

FOREIGN PATENT DOCUMENTS

| | | |
|---|---|---|
| EP | 2075022 A1 | 7/2009 |
| GB | 1190877 A | 5/1970 |
| WO | 2007073211 A1 | 6/2007 |
| WO | 2009032932 A1 | 3/2009 |

OTHER PUBLICATIONS

Communication from PCT/US2010/057985, dated Apr. 7, 2011.

*Primary Examiner* — Loan H Thanh
*Assistant Examiner* — Nyca T Nguyen
(74) *Attorney, Agent, or Firm* — Lerner, David, Littenberg, Krumholz & Mentlik, LLP

(57) ABSTRACT

A manually operated ventilating element such as a bellows for administration of artificial respiration, for example, during anesthesia, has wall sections or pleats of different diameters. When the element is actuated through a small stroke length, the smaller section is actuated. A small volume of gas is delivered and the change in delivered volume per unit stroke length is small, so that the operator can precisely control the delivered volume. When the element is actuated through a larger stroke length, a larger volume per unit stroke length is delivered. The same element can be used to treat children and adults.

9 Claims, 8 Drawing Sheets

(56) References Cited

U.S. PATENT DOCUMENTS

| | | |
|---|---|---|
| 5,520,173 A | 5/1996 | Kuhn |
| 5,787,880 A | 8/1998 | Swanson et al. |
| 5,809,996 A * | 9/1998 | Alldredge ................ 128/200.23 |
| 2003/0010336 A1 * | 1/2003 | Vito ......................... 128/200.22 |
| 2006/0180146 A1 | 8/2006 | Thompson et al. |
| 2008/0015475 A1 | 1/2008 | Lau et al. |
| 2009/0145437 A1 | 6/2009 | Halpern |
| 2011/0132359 A1 * | 6/2011 | Poree ....................... 128/203.21 |

* cited by examiner

VENTILATING ELEMENT, SYSTEM, AND METHODS

CROSS-REFERENCE TO RELATED APPLICATIONS

This application claims the benefit of the filing date of U.S. Provisional Patent Application No. 61/307,066 filed Feb. 23, 2010, the disclosure of which is hereby incorporated herein by reference.

BACKGROUND OF THE INVENTION

The present invention relates to breathing systems such as anesthesia systems, ventilating elements for use in such systems, and methods of administering ventilation.

A typical anesthesia system includes a breathing circuit for delivering a gas mixture including air or another oxygen-containing gas and an inhalation anesthetic agent to the patient. The breathing circuit typically includes one or more conduits connected to a mask or tube which communicates with the patient's lungs. The breathing circuit also may include elements such as devices for adding anesthetic agent to the gas mixture, adsorbers for removing undesirable constituents from the gas mixture, and the like. The conduits commonly are arranged in a closed loop, so that gas mixture continually circulates in the loop, with some or all of the exhaled gas passing back to the patient, in admixture with fresh gasses. The circuit is commonly provided with check valves which allow flow in one direction along the circuit but block flow in the opposite direction.

In many cases, the patient cannot breathe spontaneously. Therefore, the anesthesia system typically also includes an element referred to herein as a "ventilating element" defining a chamber of variable volume in communication with a conduit of the breathing circuit. The ventilating element can be repeatedly expanded to draw in gas and then forcibly collapsed to expel the gas into the conduit. When the ventilating element is collapsed, the check valves in the circuit assure that the gas expelled from the ventilating element is directed to the patient. This provides a positive pressure which overcomes the natural elastic recoil of the lungs and chest wall, and overcomes the resistance of patient's airways, and thus forces the gas into the lungs to provide inhalation. This procedure is commonly referred to as "positive pressure ventilation."

A mechanical system can be used to provide positive pressure ventilation by automatically actuating the ventilating element. However, in many cases it is desirable to actuate the ventilating element manually. A skilled operator such as an anesthesiologist, anesthetist or other medical professional can provide the correct volume of the gas mixture for inhalation by feel, without the cost, complexity and reliability issues associated with an automatic ventilation system. Merely by way of example, manual ventilation is particularly advantageous where anesthesia must be administered in a setting where resources are limited as, for example, in remote rural regions of the world or in areas affected by natural disasters.

Ventilating elements which can be actuated manually include bags and bellows. A bag may be a soft, balloon-like structure which is normally slack, so that the bag is inflated by the gas pressure in the breathing circuit. Alternatively, a bag may have resilient walls which tend to return the bag to an inflated condition and thus draw gas into the bag. The bag may have one open end which is connected to the breathing circuit, or may have separate gas intake and gas outlet openings at opposite ends. The operator squeezes the bag to collapse it and provide positive pressure for inhalation. A bellows typically has a closed end, an open end and a series of pleats between the ends. The open end is connected to a conduit of the breathing circuit for entry and exit of gas. The operator can manually expand and collapse the bellows by moving the closed end towards and away from the open end.

The volume of gas delivered to the patient during each respiratory cycle, commonly referred to as the "tidal volume" must be selected to match the lung capacity of the patient. Children require considerably smaller tidal volumes than adults. If a ventilating element intended for use with adults is used to deliver positive pressure ventilation to a small child, the operator may accidentally deliver an excess tidal volume or excess positive inflating pressure to the child. When using a system equipped with a bag, the operator normally must select a bag having the correct size for the patient. This can lead to accidents if the wrong bag is installed.

Systems using bellows typically employ only one size of bellows. These bellows are sized to provide the correct tidal volume for an adult when operated through a reasonable stroke. To provide the correct tidal volume for a small child, the operator must use a very short stroke. In these conditions, it is difficult for the operator to estimate and control the volume administered. This increases the difficulty and risk of the procedure.

Kuhn, U.S. Pat. No. 5,520,173 ("the '173 patent") discloses a tubular ventilating element having two open ends and an axis extending between these ends. The element can be connected between conduits of a breathing circuit. The element has sections of different diameters. The element is resilient, and returns to a fully-expanded condition under the influence of its own resilience. The operator can pump gas through the element by squeezing the element in directions transverse to the axis. According to the '173 patent, the operator can pump a large volume of gas by squeezing a large-diameter section of the element, or pump a small volume of gas by squeezing a small-diameter section of the element. Such an element requires an unnatural control action by the operator, is fatiguing for the operator, and suffers from other drawbacks.

Thus, despite considerable effort in the art, further improvement would be desirable.

BRIEF SUMMARY OF THE INVENTION

One aspect of the invention provides a ventilating element for use with a breathing circuit as, for example in anesthesia apparatus. The ventilating element according to this aspect of the invention desirably includes a hollow body having a closed end, an open end and a plurality of wall sections between the ends the body defining an interior space. The wall sections are movable in an output direction toward the closed end to diminish the volume of the interior space and movable in an intake direction away from the closed end to increase the volume of the interior space. The wall sections most preferably include one or more first wall sections having cross-sectional areas and one or more second wall sections having cross-sectional areas less than the cross-sectional areas of the first wall sections. For example, the body may be a bellows, and the wall sections may be pleats of the bellows, the pleats including one or more large-diameter pleats constituting the first walls sections and one or more small-diameter pleats constituting the second wall sections. The body desirably is constructed and arranged so that an operator can selectively either (i) manually move only the second wall sections to pump a relatively small volume of gas, or (ii) manually move the first wall sections to pump a relatively large volume of gas.

A further aspect of the invention provides breathing apparatus which includes a ventilating element defining an interior space. The apparatus according to this aspect of the invention desirably also includes a manually-movable control element movable over a stroke between a full-output position and a full-intake position, the control element being mechanically connected to the ventilating element so that the volume of the interior space increases with movement of the control element toward the full-intake position and decreases with movement of the control element toward the full-output position. Most preferably, the ventilating element, control element and the connection between the ventilating element and control element are constructed and arranged such that when the control element is near the full output position a ratio between change in volume of the interior space and movement of the control element is has a first magnitude, whereas near the full intake position, the ratio has a second magnitude, larger than the first magnitude.

Still further aspects of the invention provide methods of administering positive pressure ventilation.

DETAILED DESCRIPTION

Figure 1:
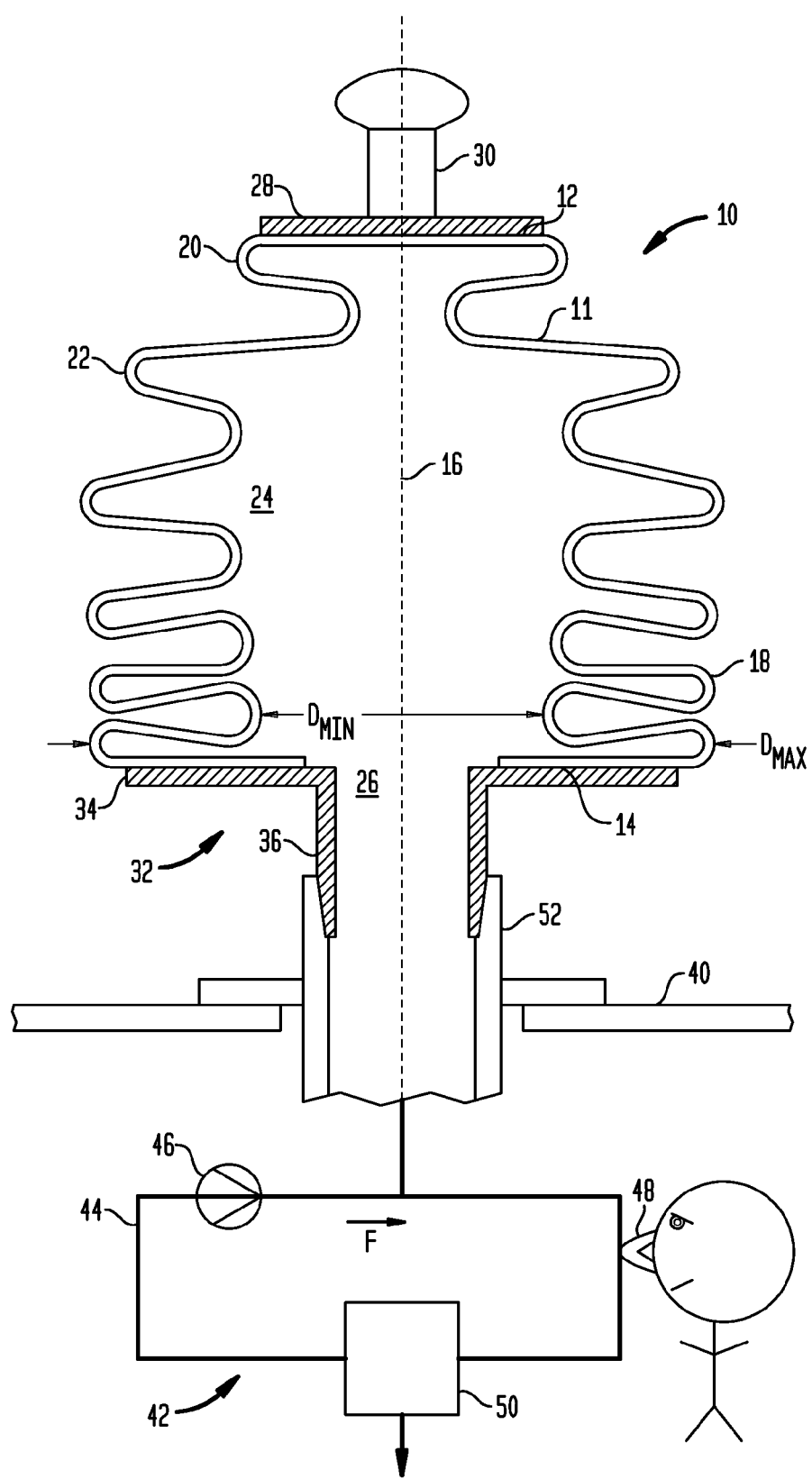
FIG. 1 is a partially sectional, partially schematic view of a system in accordance with one embodiment of the invention.

A system according to one embodiment of the invention includes a ventilating element 10 in the form of a bellows. The bellows is formed as a unitary hollow body 11 of a flexible material, such as a flexible polymer as, for example, silicone rubber of about 40 to about 65 Shore A Durometer. Body 11 has a closed end 12, an open end 14 and an axis 16 extending between the ends. The body includes first wall sections in the form of four first pleats 18 of circular cross-section encircling axis 16 adjacent open end 14. When fully collapsed in the axial direction, each of the first wall sections or pleats 18 has a major inside diameter $D_{MAJ}$ of about 16 cm and a minor inside diameter $D_{MIN}$ of about 10 cm. The mean interior cross-sectional area within each first pleat 18 in a plane perpendicular to axis 16 is given by $(\pi[D_{MAJ}^2 - D_{MIN}^2])/4$, is about 122 cm². Body 11 further includes one or more second wall sections in the form of a second pleat 20 encircling axis 16 adjacent closed end 12. Second pleat 20 has a major diameter of about 8 cm, a minor diameter of about 3 cm, and a mean interior cross-sectional area of about 43 cm². Stated another way, the second wall section or pleat 20 has dimensions transverse to axis 16 smaller than the corresponding dimensions of the first wall sections or pleats 18, and has a smaller cross-sectional area than the first wall sections. Body 11 further includes one or more third wall sections or pleats 22 disposed between the first wall sections and the second wall sections, the third wall sections having diameters and cross-sectional area less than those of the first wall sections 18 but greater than those of the second wall section 20. The wall sections 18, 20 and 22 cooperatively enclose an interior space 24 between the ends 12 and 14. The body has a port 26 at the open end communicating with interior space 24.

Ventilating element 10 includes a closed-end plate 28 affixed to the closed end 12 of the body. The plate extends transverse to axis 16 of body 10, and is bonded to the material of the body plate 28 extends outwardly from the axis to the juncture of the second pleat 20 with the closed end of the body. Plate 28 is formed from a relatively rigid material such a metal, and has stiffness such that in service, deflection of the plate is negligible. A handle 30 is attached to plate 28, and thus to the closed end 12 of the body. The handle projects along axis 16 away from body 11.

The ventilating element further includes a fitting 32. The fitting includes a closed end plate 34 bonded to the closed end of body 11 and extending transversely to axis 16 to the vicinity of a first end pleat 18. Plate 34 has a hole aligned with the opening 26 in the body. Fitting 32 further includes a connector 36 fixed to plate 34. The connector communicates with the interior space 24 within body 11 through hole 26. The connector is arranged to engage a mating fitting of an anesthesia system as discussed below. In the particular example depicted in FIG. 1, connector 36 has a male tapered end to mate with a female tapered fitting. However, this is merely illustrative. For example, the connector may have a threaded configuration to engage a corresponding threaded fitting, or any other configuration which can establish a mechanical connection to the mating fitting, as well as establish communication with the other components of the system discussed below.

In addition to the ventilating element 10, the anesthesia system includes an anesthesia machine having a chassis 40 as well as a breathing circuit 42. Breathing circuit 42 includes a series of communicating conduits 44 and one or more check valves 46 which allow flow through the conduits in a forward direction F. The conduits are connected to a patient interface device such as a mask 48, endotracheal tube or other conventional device for communicating with the patient's respiratory tract. The breathing circuit also includes one or more conventional elements 50 for regulating the composition of the gas flowing within the conduits as, for example, by adsorbing exhaled gas constituents, adding anesthetic agent to the gas, and discharging waste gas from the circuit. The breathing circuit and the elements constituting the breathing circuit may be of conventional construction. Numerous breathing circuits are known in the art, and any such circuit may be employed. Although most conventional breathing circuits have conduits arranged in a substantially closed loop for recirculation of at least some of the gas, this is not essential. The anesthesia machine may include known components for controlling and monitoring conditions in the breathing circuit. A connector 52 is physically secured to the chassis 40 of the anesthesia machine, and communicates with one of the conduits 44 of breathing circuit 44. Connector 52 may be provided as a permanent fitting of the anesthesia machine, or may be provided as part of the breathing circuit, and secured in place on the anesthesia machine chassis by appropriate fasteners (not shown).

The connector 36 of ventilating element 10 is connected to connector 52, so that the ventilating element is mechanically secured to the machine chassis 40, and so that the interior space 24 within the body 11 of the ventilating element is in communication with the breathing circuit. The body 11 is disposed above the chassis, with the closed end 12 and handle 30 pointing upwardly in the normal gravitational frame of reference, and with the open end 14 of the body supported by the open end plate 34 of fitting 32. In a rest or idle condition depicted in FIG. 2, with no manual actuation, the body 11 is in a fully-collapsed condition where the interior space 24 (FIG. 1) has minimum volume. In this fully-collapsed condition, all of the pleats or wall sections 18, 20, and 22 are fully advanced toward the open end of the body. The body is retained in this condition by the weight of the body itself, and by the weight of the closed end plate 28 and handle 30. The normal or undistorted shape of the body 11 itself may be the fully-collapsed condition, so that the body tends to return to this condition under the influence of its own resilience.

In a method according to an embodiment of the invention, the breathing circuit and anesthesia machine are actuated in the conventional manner to pass a gas mixture through the breathing circuit and to the patient. While the patient is breathing spontaneously, the patient's own respiratory effort circulates gas within the breathing circuit 42. The bellows remains in the rest condition of FIG. 2.

Figure 2:
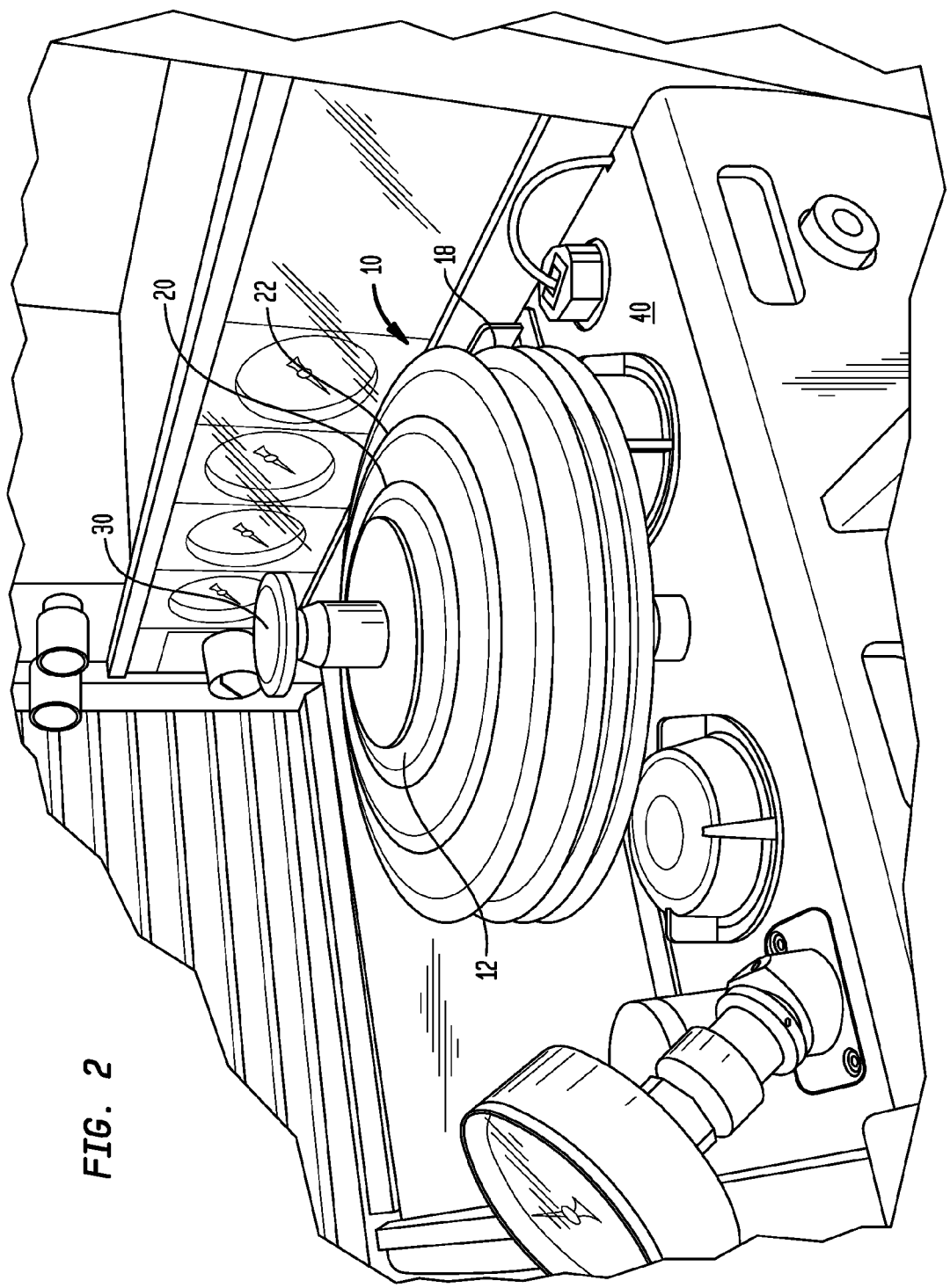
FIG. 2 is a perspective view depicting a portion of the system of FIG. 1 in an idle condition.

If the patient requires positive pressure ventilation, the operator can actuate the ventilating element. The operator moves the handle 30, and hence the closed end 12 of the body, with a component of motion in an intake direction, upwardly away from the open end 14. As the operator moves the closed end in the intake direction, one or more of the pleats expand axially, so that one or more of the pleats or wall sections also move in the intake direction to increase the volume of the interior space within the body and draw gas into the body. The operator then advances the closed end 12 of the body downwardly, in an output direction toward the closed end, to diminish the volume of the interior space and expel gas from the body. In cooperation with the check valves incorporated in the breathing circuit, this action pumps gas in the forward direction F (FIG. 1). Thus, every time the operator advances the closed end in the output direction, the pressure in the conduit section between a check valve 46 and the patient interface 48 is momentarily increased. This momentary pressure overcomes the elastic recoil of the patient's chest and lungs, and thus forces gas into the lungs to produce an artificial inhalation. This action is repeated cyclically.

The change in volume of the interior space during each cycle, and hence the volume of gas delivered to the patient in each inhalation, varies directly with the length of the stroke. Moreover, the configuration of the ventilating element provides a progressive change in the relationship between delivered gas volume and stroke length as explained below.

Figure 3:
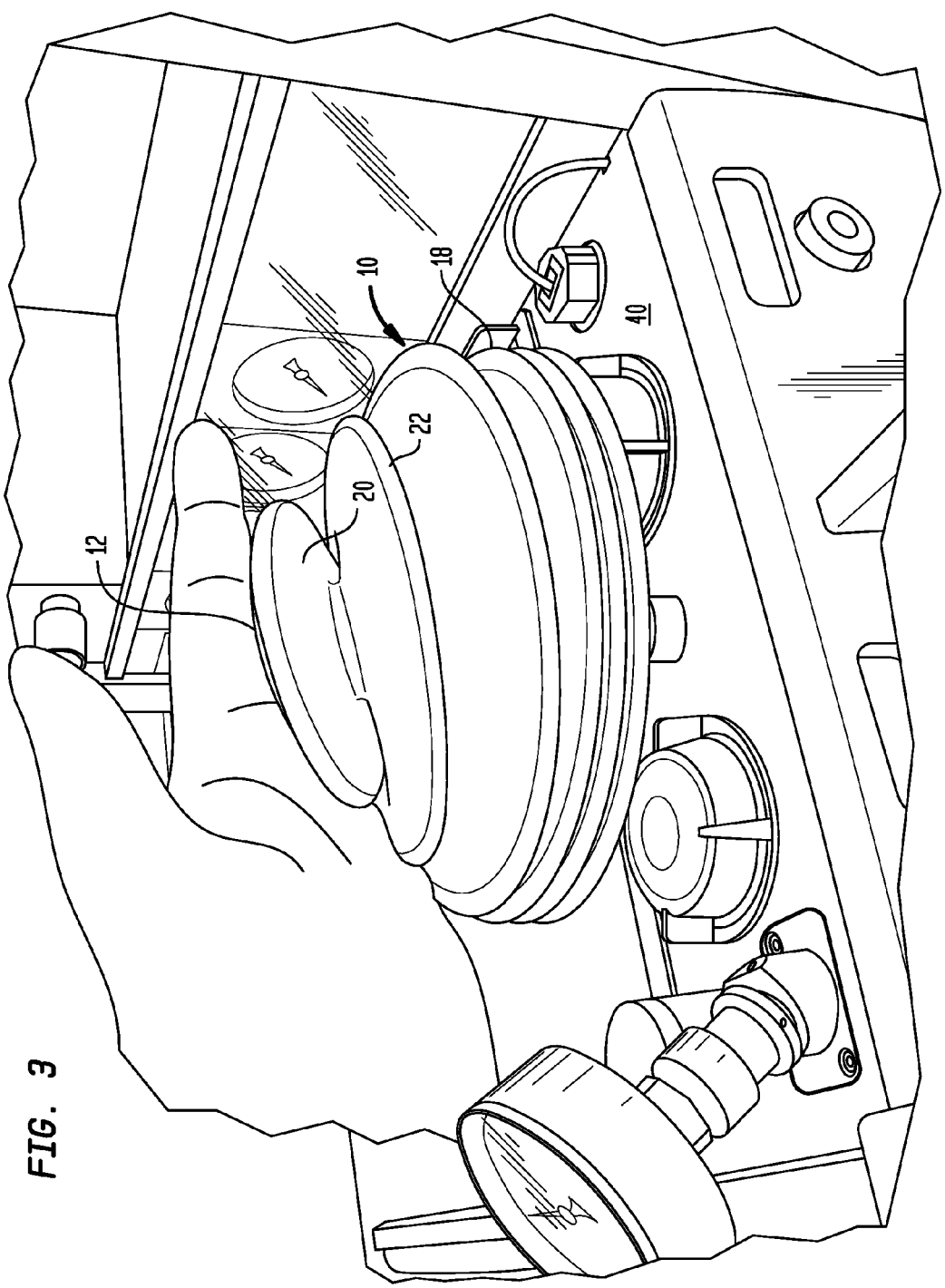
FIG. 3 is a view similar to FIG. 2 depicting the system of FIGS. 1 and 2 in one operating condition.
Figure 4:
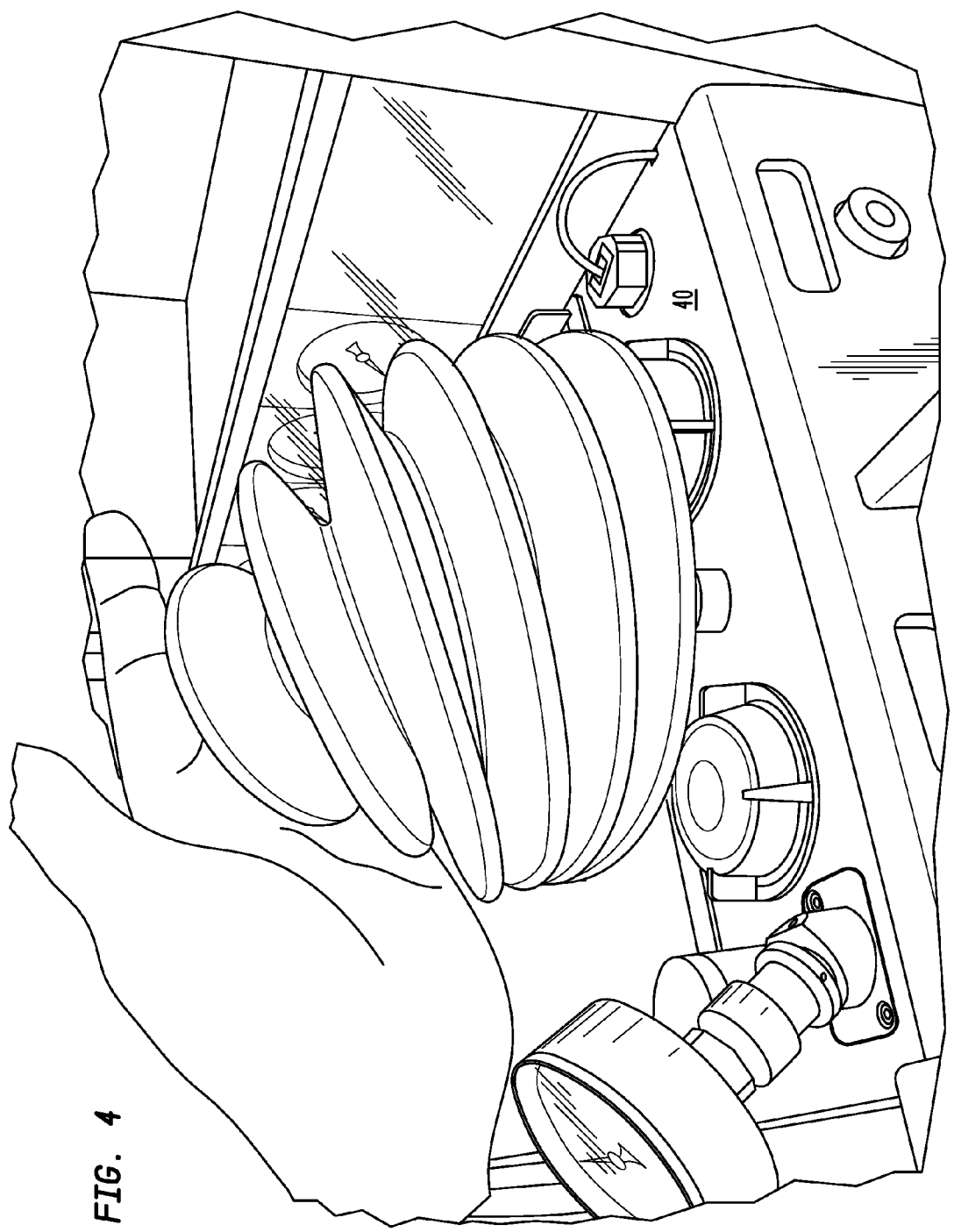
FIG. 4 is a view similar to FIG. 3 depicting the system of FIGS. 1-3 in another operating condition.

As the closed end 12 moves in the intake direction, the second wall section or smallest pleat 20 is the first to move in the intake direction, followed by the third wall section or intermediate-diameter pleat 22, and finally by the first wall sections or first-diameter pleats 18. Stated another way, the upward force required to expand the larger pleats against the influence of gravity and the resilience of the body is greater than the upward force required to expand the smaller pleats. The larger pleats thus tend to remain collapsed until the smaller pleats have been fully expanded. This pattern of expansion can be further assured by physically restraining the larger pleats or first wall sections against movement in the intake direction. The operator may provide such restraint naturally, by resting the heel or palm of his or her hand on the larger pleats while lifting the handle with the fingers of the same hand as shown in FIG. 3. In the condition seen in FIG. 3, the closed end has been moved upwardly to a sufficient extent to expand the smallest pleat 20 and intermediate pleat 22, while leaving the first or largest pleats in the same state as in the rest condition, and thus substantially contracted. In the condition seen in FIG. 4, the operator has continued the upward stroke by lifting his or her palm as well as the fingers. The closed end has been moved further in the intake direction, so that all of the pleats are at least partially expanded.

For a very small stroke, the delivered volume is approximately equal to the product of the stroke length and the cross-sectional area of the second wall section or smallest pleat 20. Because this cross-sectional area is small, the operator can make small adjustments in the delivered volume easily, to provide precise control of the delivered volume as required for a small child. As the stroke length increases and the intermediate pleat or third wall section 22 is involved in the pumping action, the change in delivered volume per unit change in stroke length increases. This progressive change continues as the stroke length further increases as the largest pleats or first wall sections 18 are involved. Thus, at large stroke lengths and large delivered volumes, the change in delivered volume per unit change in stroke length is at a maximum. Thus, the operator can deliver and control the large volumes required for treatment of an adult. This progressive change occurs without the need for the operator to select or adjust different controls, or actuate different parts of the ventilating element. Operators familiar with the operation of conventional bellows ventilating element can use the system with minimal training or practice. It is not necessary to select different ventilating elements for different patients.

Numerous variations and combinations of the features discussed above can be used. For example, the number of pleats of each size can be varied. The body may include only two different sizes of wall sections or pleats. The end plates 28 and 34 may be embedded in the material of the body 11, or may be omitted entirely if the end regions of the body have sufficient stiffness. The ventilating element may be permanently affixed to one or more of the conduits constituting the breathing circuit.

The ventilating element can be used to provide ventilation in applications other than anesthesia. For example, the ventilating element may be using in conjunction with a mask or endotracheal tube, and with one or more check valves, to provide positive pressure ventilation without anesthesia. In such an application, the ventilating element may be supported by the patient as, for example, where the ventilating element is mounted on a mask placed over the patient's face. Also, the ventilating element can be held by the operator. Thus, the term "breathing apparatus" as used herein should be understood as referring to apparatus which is used to facilitate respiration of a human or animal subject, with or without administration of anesthesia.

Figure 5:
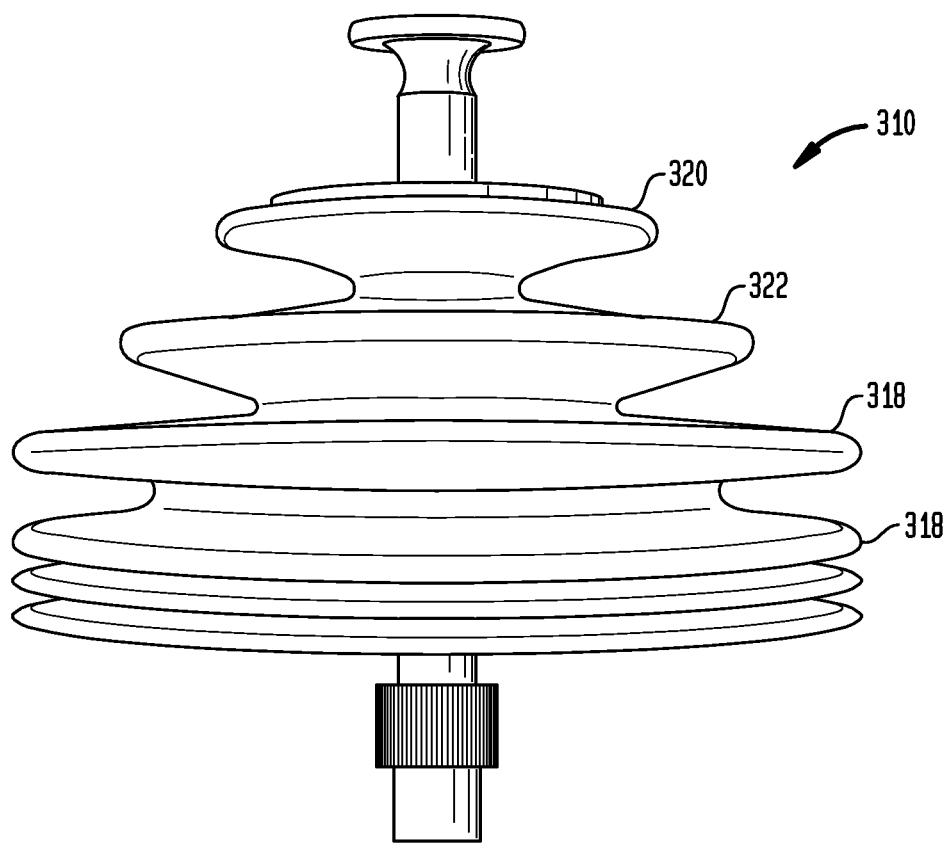
FIG. 5 is a diagrammatic elevational view depicting an element in accordance with a further embodiment of the invention.

A ventilating element 310 according to a further embodiment of the invention, shown in FIG. 5, is identical to the ventilating element of FIGS. 1-4, except that the ventilating element is biased to a rest condition which is intermediate between a fully-expanded condition and a fully-collapsed condition. In this rest condition, the second wall section or smallest pleat 320, the third wall section or intermediate pleat 322, and one of the first wall sections or largest pleats 318 are partially expanded, whereas the remaining first wall sections or largest pleats 318 are fully collapsed. A spring (not shown) may be provided inside the interior volume of the bellows to bias the bellows to this rest condition. Alternatively or additionally, the bellows may be formed so that the resilience of the bellows biases the bellows to this rest condition. This rest position helps the operator to grasp the bellows and start drawing gas in, and further reduces operator fatigue. Moreover, this partially-expanded rest position facilitates monitoring of breathing during spontaneous respiration because the bellows will move up and down with each breath. Further, the bellows with a partially-expanded rest condition is more intuitive for the first time user to grasp and move.

Figure 6:
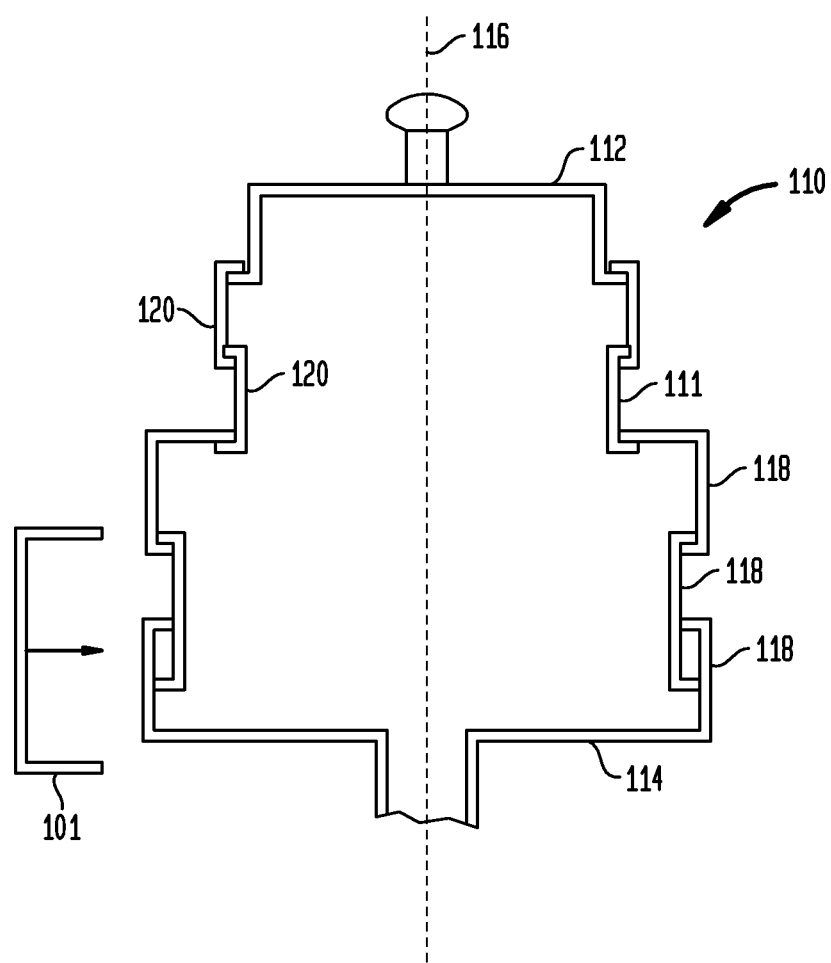
FIG. 6 is a diagrammatic sectional view depicting an element according to a further embodiment of the invention.

A ventilating element 110 according to a further embodiment of the invention (FIG. 6) includes a body 111 having first wall sections 118 in the form of relatively large-diameter rigid tubular elements telescopically engaged with one another. The first wall section closest to the open end 114 of the body is affixed to the open end. The other first wall sections can slide towards and away from the closed end 114 of the body. The body also includes second wall sections 120 in the form of smaller-diameter rigid tubular elements telescopically engaged with one another. The second wall section 120 closest to the closed end 112 is affixed to the closed end, whereas the second wall section 120 closest to the open end 114 is telescopically engaged in one of the first wall sections 118. Appropriate low-friction seals (not shown) such as sliding seals or rolling membrane seals are provided between adjacent wall sections. In this embodiment as well, the ventilating element can be actuated by moving the closed end toward and away from the open end, so that the wall sections also move towards and away from the open end 114. Here again, the wall sections operate progressively, so that only the smaller, second wall sections move in short strokes. The larger, first wall sections can be manually restrained as discussed above. Alternatively, a clip 101 can be placed around the first wall sections to retain them in a fully advanced condition, close to the open end, when small delivered volumes are desired. The clip can be removed to allow longer strokes and delivery of larger volumes. Such a clip can be used with a bellows as discussed above, to retain the larger pleats. A weight can be used in place of a clip.

In each of the embodiments discussed above, the closed end of the ventilating element and the handle constitute a control element which can be manually moved, and the ventilating element provides a progressively varying relationship between movement of the control element and change in the volume of the interior space within the control element. Near the full output end of the stroke, where the volume of the interior space is at a minimum, the change in volume per unit movement of the control element is relatively small, whereas near the full intake end of the stroke, where the volume of the interior space is at a maximum, the change in volume per unit movement of the control element is relatively large. A similar progressive relationship can be provided using a ventilating element of uniform cross-sectional area, such as a bellows having uniform diameter over its length or a piston and cylinder of uniform diameter, if a mechanical linkage is provided between the control element and the movable part of the ventilating element, the mechanical linkage being arranged so that the ratio of distance traveled by the movable part of the ventilating element to distance traveled by the control element varies over the stroke of the control element. The mechanical linkage is configured such that the ratio is relatively small near the full output end of the stroke and relatively large near the full input end of the stroke.

Figure 7:
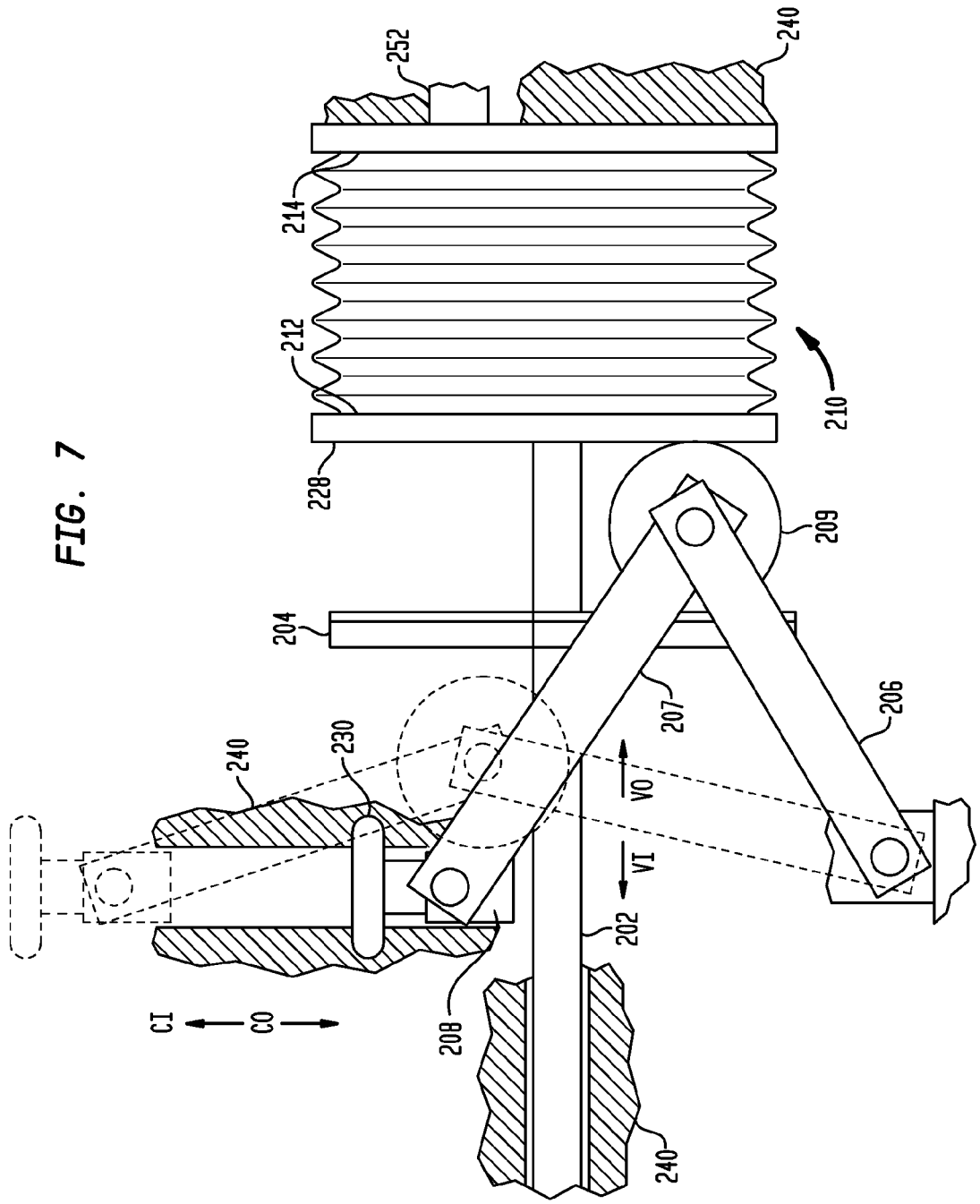
FIG. 7 is a schematic view depicting portions of an apparatus according to a further embodiment of the invention.

Merely by way of example, the apparatus shown in FIG. 7 has a ventilating element in the form of a bellows 210 with uniform pleats, and has a chassis 240, portions of which are depicted schematically. The open end 214 of bellows 210 is fixed to chassis 240. The interior space within the bellows communicates, through a connector 252, with the breathing circuit (not shown). The closed end 212 of the bellows is attached to a plate 228 which in turn is attached to a rod 202. Rod 202 is slidably mounted to chassis 240 for movement in a ventilating element intake direction VI and an opposite ventilating element output direction VO. Another plate 204 is also attached to the rod. A first link 206 is pin-jointed to chassis 240 at one end and pin-jointed to a second link 207 at the opposite end. A roller 209 is mounted to the pin-jointed ends of links 206 and 207. Roller 209 is disposed between plates 228 and 224. The end of link 207 remote from link 206 is pin-jointed to a slider 208 which in turn is slidably mounted to chassis 240 for movement in a control element intake direction CI and opposite control element output direction CO. Directions CI and CO are transverse to directions VI and VO. A control element such as a handle 230 is mounted to slider 208.

In the full output position depicted in solid lines in FIG. 7, bellows 210 is fully collapsed and the volume of the interior space is at a minimum. As the operator moves control element 230 in direction CI, the mechanism moves to the full intake position depicted in broken lines. Near the full output position depicted in solid lines, roller 209, and hence the closed end 212 of bellows 210, moves only a small distance in direction VI or VO for each unit of movement of control element 230 in direction CI or CO. Near the full intake position, the roller 209, and hence the closed end 212 of the bellows, moves through a larger distance in direction VI or VO for each unit of movement in direction CI or CO.

The mechanism depicted in FIG. 7 is merely exemplary. Many other linkages can provide similar progressively varying ratios between movement of elements. These include cam and follower linkages, linkages using a belt or string wrapped on a pulley of non-uniform diameter, and linkages including gears or frictionally-engaged surfaces of non-uniform diameters. These and other mechanisms can be used.

Figure 8:
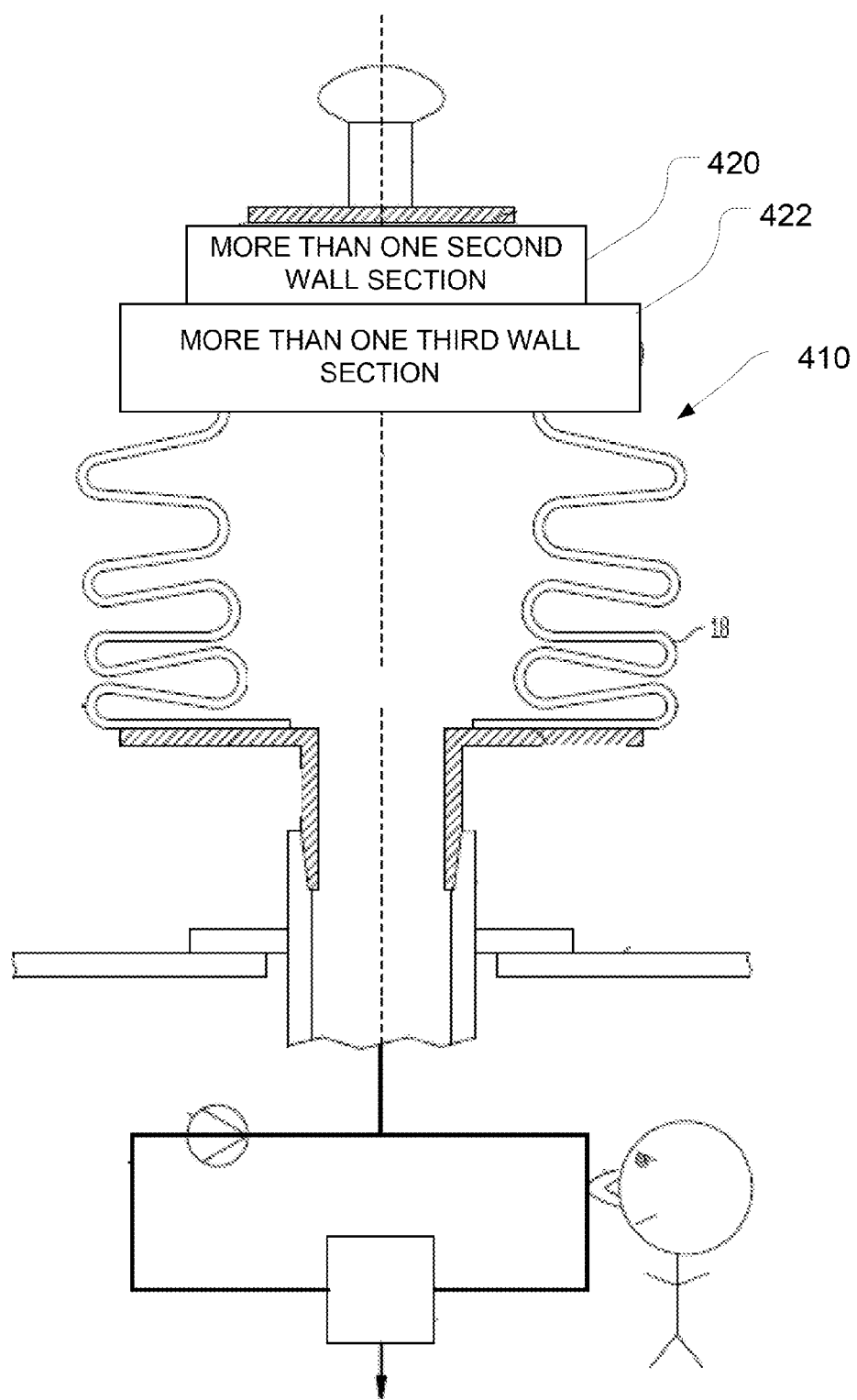
FIG. 8 is a view similar to FIG. 1 but depicting a system according to a further embodiment of the invention.

The system depicted in FIG. 8 is identical to the system depicted in FIG. 1, except that FIG. 8 schematically shows that the ventilating element 410 has more than one second wall section 420 and more than one third wall section 422.

As these and other variations and combinations of the features discussed above can be utilized without departing from the present invention, the foregoing description of the preferred embodiments should be taken by way of illustration rather than by way of limitation of the invention as defined by the claims.

I claim:

1. A ventilating element for use with a breathing apparatus, the element comprising a hollow body having a closed end, an open end and a plurality of wall sections between the ends, the body defining an interior space, the wall sections being movable in an output direction toward the open end to diminish the volume of the interior space and movable in an intake direction away from the open end to increase the volume of the interior space, the element further including a fitting disposed at the open end, wherein the wall sections include a plurality of first wall sections disposed adjacent the open end, the plurality of first wall sections having a common first cross-sectional area and one or more second wall sections disposed adjacent the closed end, the one or more second wall sections having a second cross-sectional area less than the first cross-sectional area, the ventilating element further including a closed-end plate disposed at the closed end of the body and mechanically connected to one of the one or more second wall sections adjacent the closed end, whereby the wall sections can be moved by manipulating the closed end plate, and a handle mechanically connected to the closed end plate, wherein the fitting is constructed and arranged to connect the body with the breathing apparatus so that the open end of the body communicates with the breathing apparatus and so that the open end of the body is constrained against movement, and wherein the body is constructed and arranged so that without the need for an operator to select or adjust different controls, the operator can selectively either (i) manually move only the second wall sections without moving the first wall sections to pump a relatively small volume of gas per unit length of motion, or (ii) manually move the first wall sections to pump a relatively large volume of gas per unit length of motion.

2. A ventilating element as claimed in claim 1 wherein the body has an axis extending between the ends and the wall sections surround the axis.

3. A ventilating element as claimed in claim 1 wherein the fitting includes an open end plate mechanically connected to one of the plurality of first wall sections adjacent the open end.

4. A ventilating element as claimed in claim 1 wherein the wall sections include pleats formed from a flexible material.

5. A ventilating element as claimed in claim 1 wherein the first cross-sectional area is about 100 to about 160 cm$^2$ and the second cross-sectional area is about 30 to about 60 cm$^2$.

6. A ventilating element as claimed in claim 1 wherein the wall sections include one or more third wall sections disposed between the first wall sections and the second wall sections, the third wall sections having cross-sectional area less than the first cross-sectional area but greater than the second cross-sectional area.

7. A breathing system including a breathing circuit, a machine chassis and a ventilating element as claimed in any of claim 1, 2, or 3 through 5, the element being mechanically connected to the machine chassis so that the interior space within the body is in communication with the breathing circuit, so that the open end of the body is fixed to the machine chassis and so that the ventilating element is supported by the breathing machine chassis.

8. A system as claimed in claim 7 wherein the closed end of the body is disposed above the open end.

9. A ventilating element for a breathing apparatus comprising a unitary bellows defining an interior space, the bellows having a closed end, an open end, an axis extending between the ends and a plurality of pleats formed from a flexible material extending around the axis between the ends, the pleats including a plurality of large pleats having a common first diameter disposed adjacent the open end and one or more small pleats having a second diameter less than the first diameter disposed adjacent the closed end, the element further including a closed end plate disposed at the closed end of the bellows and mechanically connected to one of the one or more small pleats adjacent the closed end, and a handle mechanically connected to the closed end plate;

the element further including a fitting disposed at the open end and mechanically connected to one of the plurality of large pleats adjacent the open end, the fitting being constructed and arranged to connect the bellows with the breathing apparatus so that the open end of the bellows communicates with the breathing apparatus and so that the open end of the bellows is constrained against movement, the bellows being constructed and arranged so that an operator can selectively either (i) manually move only the small pleats without moving the large pleats to pump a relatively small volume of gas per unit length of motion, or (ii) manually move the large pleats to pump a relatively large volume of gas per unit length of motion.

* * * * *